(12) United States Patent
Jung et al.

(10) Patent No.: US 12,201,824 B2
(45) Date of Patent: Jan. 21, 2025

(54) MICRO LEAD FOR DIRECTIONAL STIMULATION

(71) Applicant: Heraeus Deutschland GmbH & Co. KG, Hanau (DE)

(72) Inventors: Markus Jung, Hanau (DE); Thorsten Kaiser, Hanau (DE)

(73) Assignee: Heraeus Deutschland GmbH & Co. KG, Hanau (DE)

( * ) Notice: Subject to any disclaimer, the term of this patent is extended or adjusted under 35 U.S.C. 154(b) by 129 days.

(21) Appl. No.: 17/103,035

(22) Filed: Nov. 24, 2020

(65) Prior Publication Data

US 2021/0162206 A1 Jun. 3, 2021

(30) Foreign Application Priority Data

Nov. 28, 2019 (DE) ..................... 10 2019 218 477.4

(51) Int. Cl.
| | |
|---|---|
| *A61N 1/05* | (2006.01) |
| *A61B 5/25* | (2021.01) |
| *A61B 5/251* | (2021.01) |
| *A61B 5/263* | (2021.01) |
| *A61B 5/274* | (2021.01) |

(52) U.S. Cl.
CPC ................. *A61N 1/05* (2013.01); *A61B 5/25* (2021.01); *A61B 5/251* (2021.01); *A61B 5/263* (2021.01); *A61N 1/0551* (2013.01); *A61B 5/274* (2021.01); *A61B 2562/125* (2013.01); *A61N 1/056* (2013.01)

(58) Field of Classification Search
CPC ........ A61N 1/05; A61N 1/0551; A61N 1/056; A61B 5/25; A61B 2562/125; A61B 5/263; A61B 5/251
See application file for complete search history.

(56) References Cited

U.S. PATENT DOCUMENTS

| | | | |
|---|---|---|---|
| 4,270,830 A | 6/1981 | Brenner | |
| 5,555,618 A | 9/1996 | Winkler | |
| 7,122,101 B2 | 10/2006 | Gonsior | |
| 10,800,931 B2 | 10/2020 | Hendricks et al. | |
| 2002/0038139 A1 | 3/2002 | Wessman et al. | |
| 2004/0014355 A1* | 1/2004 | Osypka ................ A61N 1/056 | |
| | | | 439/502 |
| 2005/0228469 A1 | 10/2005 | Zarembo et al. | |
| 2005/0240252 A1 | 10/2005 | Boser et al. | |
| 2006/0037195 A1 | 2/2006 | Bauer et al. | |
| 2006/0168805 A1 | 8/2006 | Hegland et al. | |

(Continued)

FOREIGN PATENT DOCUMENTS

| | | |
|---|---|---|
| DE | 20016352 | 1/2001 |
| DE | 102012000125 | 7/2012 |

(Continued)

*Primary Examiner* — Pamela M. Bays
(74) *Attorney, Agent, or Firm* — Dicke, Billig & Czaja, PLLC

(57) ABSTRACT

One aspect relates to a medical electrode, having a conductor, an insulation, which surrounds the conductor at least in some sections over its entire circumference, protrusions in the insulation, electrode segments arranged between the protrusions, and insulating areas arranged between the electrode segments, wherein the electrode segments have steps, wherein the steps engage with the insulating areas.

16 Claims, 5 Drawing Sheets

(56) References Cited

U.S. PATENT DOCUMENTS

| | | | |
|---|---|---|---|
| 2006/0173262 A1* | 8/2006 | Hegland | B29C 45/14639 600/373 |
| 2008/0114230 A1* | 5/2008 | Addis | A61N 1/056 607/116 |
| 2008/0255647 A1* | 10/2008 | Jensen | A61N 1/05 607/119 |
| 2010/0198326 A1 | 8/2010 | Yong et al. | |
| 2010/0326701 A1 | 12/2010 | McDonald | |
| 2011/0130816 A1 | 6/2011 | Howard et al. | |
| 2011/0130817 A1* | 6/2011 | Chen | A61N 1/0534 607/116 |
| 2011/0196367 A1 | 8/2011 | Gallo | |
| 2011/0282420 A1 | 11/2011 | Boser et al. | |
| 2012/0203320 A1* | 8/2012 | DiGiore | A61N 1/0534 607/148 |
| 2013/0338745 A1 | 12/2013 | Ollivier et al. | |
| 2014/0107455 A1 | 4/2014 | Regnier et al. | |
| 2014/0121742 A1 | 5/2014 | Boser et al. | |
| 2014/0296951 A1 | 10/2014 | Vetter et al. | |
| 2015/0018915 A1* | 1/2015 | Leven | A61N 1/0534 607/116 |
| 2015/0021817 A1 | 1/2015 | Romero et al. | |
| 2016/0234967 A1 | 8/2016 | Choi et al. | |
| 2016/0235967 A1 | 8/2016 | Shan et al. | |
| 2017/0182310 A1 | 6/2017 | Troetzschel et al. | |
| 2019/0001118 A1 | 1/2019 | Ollivier et al. | |
| 2019/0159833 A1 | 5/2019 | Sutermeister et al. | |
| 2020/0061371 A1* | 2/2020 | Raines | A61N 1/36182 |
| 2020/0179685 A1 | 6/2020 | Jung | |
| 2020/0188679 A1 | 6/2020 | Jung et al. | |

FOREIGN PATENT DOCUMENTS

| | | |
|---|---|---|
| DE | 102018221355 | 6/2020 |
| DE | 102018221635 | 6/2020 |
| EP | 0292596 | 11/1988 |
| EP | 0808077 | 11/1997 |
| EP | 0879664 | 11/1998 |
| EP | 3185248 | 6/2017 |
| GB | 2397231 | 7/2004 |
| WO | 95/10978 | 4/1995 |
| WO | 96/18339 | 6/1996 |
| WO | 2004065098 | 8/2004 |
| WO | 2009/039427 | 3/2009 |
| WO | 2015031265 | 3/2015 |
| WO | 2017/010296 | 1/2017 |

* cited by examiner

MICRO LEAD FOR DIRECTIONAL STIMULATION

CROSS-REFERENCE TO RELATED APPLICATION

This Utility Patent Application claims priority to German Application No. 10 2019 218 477.4 filed on Nov. 28, 2019, which is incorporated herein by reference.

TECHNICAL FIELD

One aspect relates to a medical electrode and a process for producing a medical electrode of this type. An electrode of this type is suitable, for example, to output an electrical signal to the human body or to receive an electrical signal from the human body. The electrode can in particular be used for the directional stimulation, and can be used, for example, in pacemakers or neuromodulators.

BACKGROUND

In devices, which are introduced into the human or animal body, it is desirable to use structures, which are as small as possible, but which are difficult to produce due to their size. This applies in particular for medical stimulation and measuring electrodes, and in particular in the case of electrodes, which have several segments, which are electrically contact-connected separately from one another. It is desirable in many cases that individual segments can be flexibly positioned, i.e. a production process, which can be customized, if possible, is desired. A production process, which is as lean as possible in order to provide for flexibility and cost savings, is likewise desirable.

Very high emphasis is furthermore placed on the reliability of medical devices, such as, e.g., pacemakers, implantable cardioverters, defibrillators, and cardiac resynchronization devices, in particular on the lowest possible material fatigue. The individual components, in particular the contact-connections, are exposed to high loads during operation. Due to the fact that invasive surgery is usually required to introduce medical devices into the body or to remove or to replace parts thereof, a long service life of the individual components of the device is desirable in order to reduce the need for surgical procedures.

The production processes known in the prior art, for example thin film processes, often have a high complexity and include extensive and numerous process steps. Due to the very thin layers, electrodes produced via thin film processes are additionally often not stable in the long term and degrade in biological environment. The segmented electrodes known in the prior art often have a large number of components, which often have complex structures, so that the production thereof is complex and expensive. Expensive product-specific tools have to be made in many cases in order to be able to produce these electrodes, for example in the case of injection molding processes. Many electrodes and leads represent an injury risk for the patient, when they are dimensioned to be too large. Segmented electrodes often have only a small number of segments. However, a higher number of segments is often required or advantageous for certain applications. Electrodes with smaller dimensions, which have a higher number of electrode segments, often have very small electrode segment surfaces. These small electrode segment surfaces have a high impedance, so that high current densities are generated during operation. This can result in that a stimulation is less effective or that tissue, for example nerve cells, can be damaged. Further challenges of the prior art are sharp burrs on the surface of the segmented electrodes, which can represent an injury disk. Typical segmented electrodes have a diameter of more than 1.5 mm and a small number of electrode segments. Examples for this are disclosed in US 2016/0235967 A1, US 2014/0296951 A1, or US 2013/0338745 A1.

Smaller structures and a surface, which is as smooth as possible, would enable a lower injury risk of the patient and/or would provide for a better defined stimulation. It is often desirable that individual electrode segments can be positioned independently of one another on the electrode. In the case of many production processes and product, there are limitations thereby, for example when the segments are made of a common ring, which is divided into several segments only after the integration into the electrode setup. These segments can then not be positioned independently of one another. Even though an independent positioning of the individual segments is possible in other processes, the process is complex, for example because the segments have to be machine-finished very comprehensively. One example for this is disclosed in US 2011/0130816 A1, wherein the segments are initially provided as spherical parts, and are ground after the integration into the total setup in order to create a smooth surface. A process of this type is time-consuming and cost-extensive and produces a very large amount of waste of electrode material.

For these and other reasons there is a need for the present invention.

SUMMARY

One embodiment lies in solving one or several of the above-described and further problems of the prior art. For example, one embodiment provides for an improved production process for producing a segmented electrode. One embodiment furthermore provides segmented electrodes with improved characteristics.

This process is, for example, more cost-efficient and/or can be adapted more easily than processes of the prior art and/or provides products with improved properties, as described below. The improved contact-connection can show itself, for example, in a higher reliability, stability, and electrical properties. One embodiment provides, for example, a segmented electrode with a higher number and/or higher density of electrode segments. In some embodiments, an electrode is provided with a particularly smooth surface, which does not have any sharp burrs or edges.

Some embodiments use the processes and devices described herein, in particular those, which are described in the patent claims.

Embodiments will be described below.

1. A medical electrode, having
   a conductor, an insulation, which surrounds the conductor at least in some sections over its entire circumference,
   protrusions in the insulation,
   electrode segments arranged between the protrusions,
   and insulating areas arranged between the electrode segments,
   characterized in that the electrode segments have steps, wherein the steps engage with the insulating areas.
2. The electrode according to embodiment 1, having a plurality of electrode segments and a plurality of conductors, wherein different segments are in each case electrically connected to different conductors.

3. The electrode according to any one of the preceding embodiments, wherein the electrode segments have a structure, with the help of which the conductor is connected to an electrode segment.
4. The electrode according to embodiment 3, wherein the structure is an opening or a groove.
5. The electrode according to any one of the preceding embodiments, wherein the conductor is connected to an electrode segment by means of a substance-to-substance bond and/or in a positive manner.
6. The electrode according to any one of the preceding embodiments, wherein the insulating areas have a shrinkable plastic.
7. The electrode according to any one of the preceding embodiments, wherein the electrode segments, together with the insulating areas, form a continuous surface, so that the electrode has an isodiametric shape at least in the area of the electrode segments.
8. The electrode according to any one of the preceding embodiments, wherein the outer surface of the electrode segments furthermore has a structure, and/or has an increased roughness to improve the reception or output of an electrical signal.
9. The electrode according to any one of the preceding embodiments, wherein the electrode segments are arranged and configured to improve a directional reception or output of an electrical signal.
10. The electrode according to any one of the preceding embodiments, wherein the edges of the electrode segments are arranged and configured to improve the fatigue behavior of the conductor at the contact point to the electrode segments.
11. A process for producing a medical electrode, having the steps of
  providing a cable, which has an electrical conductor and an insulation, wherein the insulation surrounds the conductor at least in some sections over its entire circumference;
  partially removing the insulation, and thus forming spaces;
  providing electrode segments, wherein the electrode segments have steps;
  arranging the electrode segments in the spaces, and thus connecting the electrode segments to the insulation in a positive manner; and
  arranging an insulating material between two adjacent electrode segments, and thus forming insulating areas between the adjacent electrode segments, wherein the insulating areas engage with the steps.
12. The process according to embodiment 11, wherein the process further has the forming of a structure on the surface of the electrode segments or the roughening of the surface of the electrode segments to improve the reception or output of an electrical signal.
13. The process according to embodiment 11 or 12, wherein the partial removing of the insulation and/or the forming of a structure on the surface of the electrode segments, and/or the roughening of the surface of the electrode segments, takes place with the help of a laser.
14. The process according to any one of the embodiments 11 to 13, wherein the insulating material has a shrinkable plastic.
15. An electrode, which can be produced according to a process according to any one of embodiments 11 to 14.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

Figure 1:
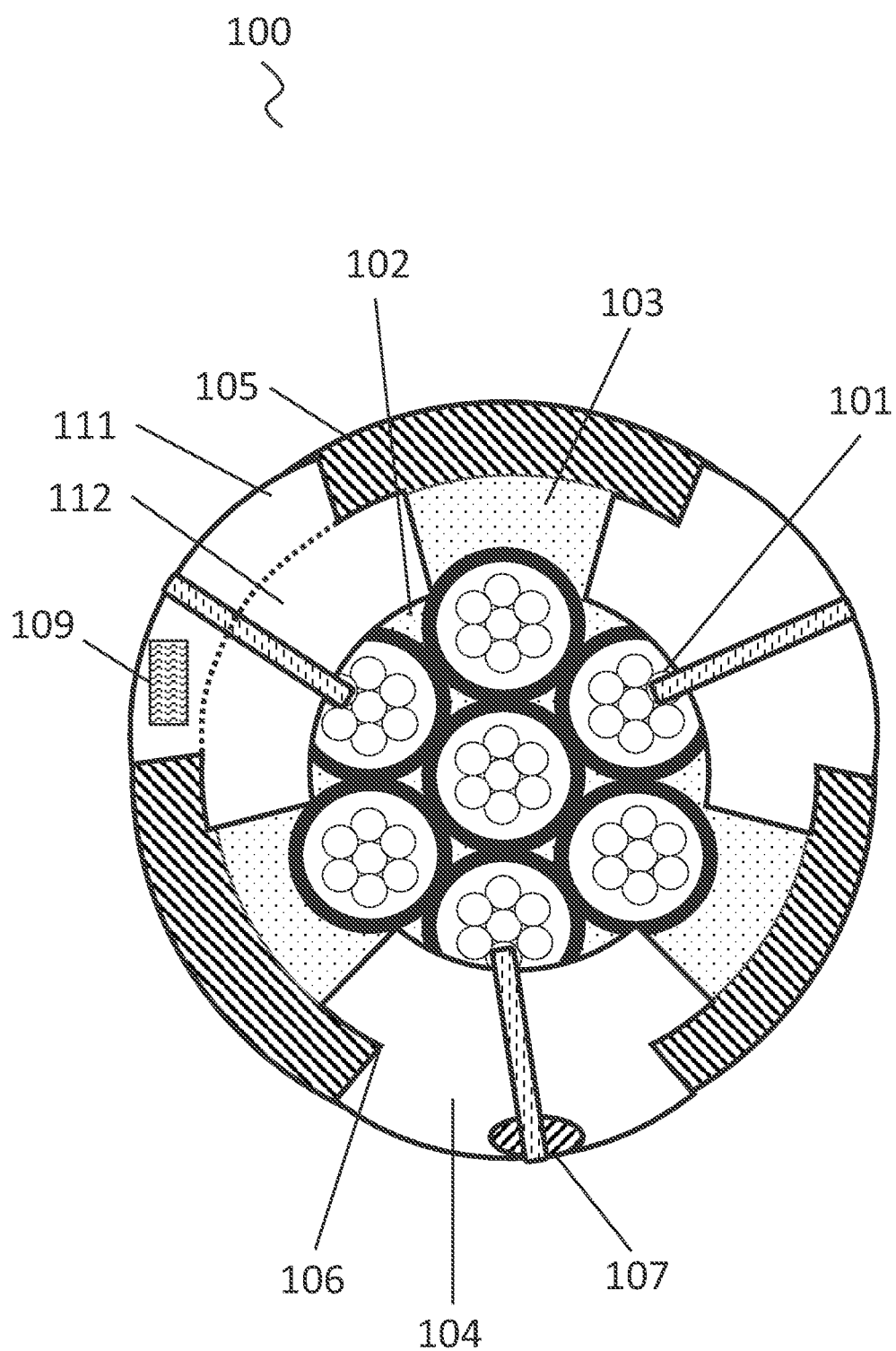
FIG. 1 illustrates a segmented electrode according to one embodiment.

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

With regard to the embodiments described herein, the elements of which "have" or "comprise" a certain feature (e.g. a material), a further embodiment is generally always considered, in which the respective element consists only of the feature, i.e. does not comprise any further components. The word "comprise" or "comprising" is used synonymously with the word "have" or "having" herein.

When an element is identified with the singular form in an embodiment, an embodiment is likewise considered, in the case of which several of these elements are present. The use of a term for an element in the plural form generally also includes an embodiment, in which only a single corresponding element is included.

Unless otherwise specified or unambiguously ruled out from the context, it is generally possible and is hereby unambiguously considered that features of different embodiments can also be present in the other embodiments described herein. It is likewise generally considered that all features, which are described herein in connection with a process, are also applicable for the products and devices described herein, and vice versa.

All of these considered combinations are not listed explicitly in all cases only for reasons of a shorter description. Technical solutions, which, as is well known, are equivalent to the features described herein, are to generally also be captured by the scope of the invention.

One embodiment relates to a medical electrode, which has a conductor, an insulation, which surrounds the conductor at least in some sections over its entire circumference, protrusions in the insulation, electrode segments arranged between the protrusions, and insulating areas arranged between the electrode segments, wherein the electrode segments have steps, wherein the steps engage with the insulating areas.

A conductor is an electroconductive structure, which is provided for the electrical connection of electrical or electronic components. A conductor can be, for example, a wire, for example an electrically insulated wire, or a conductor track. The wire can be part of a cable. A conductor can electrically connect for example an electrical pulse generator to an electrode segment, so that a signal generated by the pulse generator can be conducted to the electrode segment and can be output there, for example to the human body. A conductor can similarly connect an electrode segment to a signal detector in an electroconductive manner, so that an electrical signal received by the electrode segment can be processed by the signal detector. Several insulated wires or wire bundles can, for example, be interlaced to form a cable or can be stranded together. Different conductors within the cable can thereby be electrically insulated from one another, so that they provide for an electrical contact-connection of different electrode segments independently of one another.

The conductor can be, for example, a metal wire or a wire bundle of several wires, which are directly interlaced or stranded. In some embodiments, the conductor includes one or several of the metals Pt, Ir, Ta, Pd, Ti, Fe, Au, Mo, Nb, W, Ni, Ti, Nb, Hf, Sn, or a mixture or alloy thereof, respectively. In some embodiments, the conductor includes the alloys MP35, PtIr10, PtIr20, 316L, 301, or nitinol. The conductor can also include multi-layer material systems. The conductor in one embodiment includes MP35, Au, Ta, Pt, Ir, Pd, or Ti. In some embodiments, the wire part of the conductor consists of MP35, Au, Ta, Pt, Ir, Pd, or Ti, or alloys of these metals. In some embodiments, the conductor contains less than 3%, 2%, or less than 1% of Fe.

MP35 is a curable alloy on the basis of nickel-cobalt. A variation of MP35 is described in the industrial standard ASTM F562-13. In one embodiment, MP35 is an alloy, which includes 33 to 37% of Co, 19 to 21% of Cr, 9 to 11% of Mo, and 33 to 37% of Ni.

PtIr10 is an alloy of 88 to 92% of platinum and 8 to 12% of iridium.

PtIr20 is an alloy of 78 to 82% of platinum and 18 to 22% of iridium.

316L is an acid-resistant CrNiMo austenitic steel with approx. 17% of Cr; approx. 12% of Ni, and at least 2.0% of Mo. A variation of 316L is described in the industrial standard 10088-2. In one embodiment, 316L is an alloy, which includes 16.5 to 18.5% of Cr; 2 to 2.5% of Mo, and 10 to 13% of Ni.

301 is a chromium nickel steel with a high corrosion resistance. A variation of 301 is described in the industrial standard DIN 1.4310. In one embodiment, 301 is an alloy, which includes 16 to 18% of Cr and 6 to 8% of Ni.

Nitinol is a nickel-titanium alloy with shape memory with an orderly cubic crystal structure and a nickel portion of approximately 55%, wherein the remaining portion consists of titanium. Nitinol has good properties with respect to biocompatibility and corrosion resistance. Unless otherwise specified, all percentages herein are to be understood as percentage by mass (% by weight).

The conductor can be, for example, a wire with a diameter of 5-250 μm, more preferably 10-120 μm.

The electrode has an insulation, which surrounds the conductor at least in some sections over its entire circumference. When the electrode has several conductors, the individual conductors can be electrically insulated from one another by using this insulation, i.e. there is no direct electrical connection from one conductor to another conductor, so that the individual conductors can be addressed independently of one another. The insulation in one embodiment has a plastic, for example a plastic selected from the group consisting of polyethylene, polyurethane, polyimides, polyamides, PEEK, polyolefins, and fluorinated plastics, such as, e.g. ETFE, PTFE, PFA, PVDF, or FEP.

The thickness of the insulation can be, for example, 3 to 150 μm, more preferably 5 to 40 μm.

The insulation has protrusions. This means that the insulation has a varying thickness in the radial direction, i.e. in the direction, in which it surrounds the conductor, and/or in the axial direction, i.e. in the direction along the conductor. The areas with smaller thickness are in one embodiment arranged and configured to essentially receive the electrode segments so as to fit accurately. In one embodiment, the protrusions are produced by removing the material of the insulation. In one embodiment, the protrusions are made by pressing the electrode segments with the insulation. In one embodiment, the protrusions define the distance between the electrode segments.

The overall construction of a rod-shaped electrode can have, for example, an outer diameter of 20 to 2000 μm, more preferably 100 to 1000 μm. The cross section of the rod shape can be circular or polygonal, whereby the edges can be rounded.

The electrode segments can have a length of, for example, 50-5000 μm, more preferably 100 to 1000 μm.

The thickness, i.e. wall thickness, of the electrode segments can be, for example, 5 to 200 μm, more preferably 10-100 μm.

The radial cross sections of the electrode segments can be formed to be flat or curved, depending on the rod shape of the electrode.

The electrode segments have steps. These steps are designed in such a way that the electrode segments are wider at a point, which is arranged closer to the center of the electrode, than at another point, which is arranged farther away from the center of the electrode. The electrode segments are thus widened on the side, which is arranged towards the center of the electrode. This step can have an essentially rectangular or a rounded shape, as long as it fulfills the below-described function, i.e. stabilizes the electrode segments in the overall construction of the electrode, as described below. A rounded shape of the step can be advantageous for the stability of the electrode, as is described in more detail below. The step can define an outer part and an inner part of the electrode segment. Several steps in the electrode segment can together define an outer and an inner part of the electrode segment, in particular when they are arranged at the same radial distance, based on the center of the electrode. The outer part of the electrode segment points to the outside of the electrode or is intended for being arranged towards the outside of the electrode after the installation into the electrode. The inner part of the electrode segment points to the inside of the electrode or is intended for being arranged towards the inside of the electrode after the installation into the electrode. In one embodiment, the outer part of the electrode segment is smaller than the inner part of the electrode segment. In one embodiment, the inner part is wider than the outer part of the electrode segment, i.e. the inner part extends over a larger distance than the outer part of the electrode segment in the radial direction of the electrode. In one embodiment, the inner part and the outer part of the electrode segment form a step.

In one embodiment, the electrode segments have several steps. The electrode segments in one embodiment have steps on two opposite sides, for example in the axial or radial direction of the electrode. In one embodiment, the electrode segments in each case have steps on two opposite sides in the axial direction of the electrode. In one embodiment, electrode segments in each case have steps on four sides of the electrode segment. In one embodiment, all steps have the same geometry. In one embodiment, the steps have different geometries. In one embodiment, the steps in each case extend along a complete outer edge of an electrode segment. In one embodiment, the steps extend only partially along an outer edge of an electrode segment. In a further embodiment, the projected surface area of the electrode segments can be circular or oval, so that a circumferential step is present, which can either be formed to be circumferentially uniform or the depth of which varies over the segment circumference. In a further embodiment, the projected surface area can have an arbitrary geometry, which contributes to improving the fatigue behavior at the transition from electrode segment to insulation. This can be attained, for example, in that the projected surface area is notched on the axial sides and/or in that the formation of corners is avoided as well as all edges are rounded.

The steps of the electrode segments engage with the insulating areas. In one embodiment, the insulating areas cover the inner part of the electrode segment, i.e. the part of the step pointing to the inside of the electrode, as described above. The insulating areas in one embodiment cover the inner part of the step completely. In one embodiment, the steps and the electrode segments are arranged and set up relative to one another in such a way that they stabilize the electrode segments. When the insulating areas bear on the steps of the electrode segments towards the outside, they can prevent that the electrode segments move to the outside or that the electrode segments rotate, stabilize the position of the electrode segments in the electrode in this way, and thus hold the electrode setup together.

The electrode can have a plurality of electrode segments and/or a plurality of conductors. In one embodiment, the electrode has a plurality of electrode segments and a plurality of conductors, wherein a plurality of electrode segments is in each case connected to different conductors. In one embodiment, none of the conductors is electrically connected to several electrode segments. Each electrode segment can in each case be electrically contact-connected, for example, to exactly one other conductor. Individual electrode segments can be electrically contacted independently of one another in this way, so that the electrode segments can output and/or receive electrical signals independently of one another.

In one embodiment, the electrode segments have a structure, with the help of which the conductor is connected to an electrode segment. A structure of this type can be, for example, an essentially circular opening, a groove, or a slot.

A structure of this type can be, for example, an opening, which connects the outside of the electrode segment to the inside of the electrode segment. The terms outside and inside hereby refer to the orientation of the electrode segment with respect to the overall construction of the electrode, i.e. the inside of the electrode segment points to the center of the electrode, while the outside of the electrode segment is arranged at a distance from the center of the electrode. Such a continuous opening provides for a stable connection to an electrical conductor, for example a line wire. For this purpose, the conductor can be guided through the opening and can subsequently be connected to the electrode segment in a non-positive and/or positive manner. The free end of a conductor can be clamped, for example, into the opening and/or can be welded inside it or to it.

As used herein, the term "positive connection", or similar, refers to a form-fit or positive-locked connection, wherein two parts are held connected because they are complementary in shape, e.g. the pieces are able to engage with each other and interlock, like two pieces of a puzzle, or a lock and a key. As used herein, the term non-positive connection, or similar, refers to a force-fit or non-positive-locked connection, wherein two parts are held connected because at least one of them exerts a force on to the other one. An example of a non-positive connection is a connection formed by clamping, cramping or switching.

In this respect, reference is made to the application DE102018221355 by the same applicant, the content of which is hereby incorporated into this application by reference. It is expressly intended that protection is sought in connection with one embodiment for the structures for connecting the electrode segment to a line wire described in DE102018221355. In one embodiment, the material of the electrode segment surrounds the opening fully. This means that the opening is arranged in the electrode segment such that the line wire guided therein cannot be moved laterally out of the opening, without first moving it along the longitudinal axis of the opening. A stable and fatigue-free fastening of the conductor to the electrode segment is thus made possible. For example, the opening can essentially be arranged centrally in the wall of the electrode segment, thus in the jacket surface of the electrode or of the electrode segment, respectively. The connection between the line wire and the electrode segment and the electrode produced therefrom is thus more stable and more fatigue-free. In one embodiment, the opening thus does not contact the outer edge of the electrode segment. In another embodiment, the conductor is fastened to the edge of the electrode segment. In one embodiment, the opening extends continuously from the inside to the outside of the electrode segment. This makes it possible to completely guide a free end of the conductor through the jacket surface of the electrode segment. This provides for a particularly stable fastening of the conductor to the electrode segment. The production of this fastening can thus also be attained more easily.

The electrical conductor can thereby be guided through the opening from the inside to the outside, so that an end of the conductor is flush with the outside.

In one embodiment, the opening has a varying diameter. For example, the opening can be conical. The opening can in one embodiment have a smaller diameter on the outside than on the inside. When the opening tapers from the inside to the outside of the electrode segment, in one embodiment tapers continuously, this can lead, for example, to the improved guidance of the conductor through the opening.

The opening is guided transversely to the longitudinal axis of the electrode. The opening can extend either at right angles to the longitudinal axis of the electrode or at an angle, which differs therefrom. "Transversely" means herein that two axes do not run parallel to one another, are thus arranged at an angle to one another, which differs from 0° or 180°, for example an angle of 1° to 179°. The longitudinal axis of the opening can be arranged, for example, at an angle of 1° to 179° to the longitudinal axis of the electrode. In one embodiment, the angle is 2° to 188°, 5° to 185°, or 10° to 170°. In one embodiment, the angle is 20° to 160°. In one embodiment, the angle is 40° to 140°. In one embodiment, the angle is 80° to 110°.

At its surface, i.e. at the outside or the inside of the electrode segment, the opening can have different shapes. In one embodiment, the opening is essentially circular. In a further embodiment, the opening is essentially elliptical at the surface. In a further embodiment, the opening at the surface has the shape of a rounded triangle, the tip of which is arranged towards the free end of the conductor.

In one embodiment, the opening at the surface has a diameter perpendicular to its longitudinal direction of less than 0.2 mm. In a further embodiment, the diameter of the opening is smaller than 0.1 mm. The diameter is at least 10 micrometers. In one embodiment, the diameter of the opening is larger than the diameter of the conductor. In one embodiment, the diameter of the opening is larger than the diameter of the conductor, or larger than the diameter of the thinnest wire of the conductor.

In one embodiment, the electrode segment includes several openings. These openings can extend essentially parallel to one another or at an angle to one another with respect to their respective longitudinal axis. The longitudinal axis of the opening runs from the inside to the outside of the electrode segment.

In one embodiment, the opening has a stop to hold one end of the conductor, in one embodiment the free end. For example, the conductor can be guided such that it abuts against the stop. A better fixation of the conductor can be attained thereby. In one embodiment, an electrode segment includes a further opening, for example a total of 2, 3, 4, 5, 6, 10, or more than 10 openings.

Further structures and processes known from the prior art can furthermore be used to connect an electrode segment to the conductor. The structures and processes described and illustrated for example in US 2011/0130816 A1, in particular FIG. 4, FIG. 5B, and FIG. 6, can be used, which are hereby incorporated completely by reference.

Connection of the Electrode Segment to the Conductor

The conductor can be connected to the electrode segment in a positive manner and/or by using a substance-to-substance bond. A substance-to-substance bond can be attained, for example, by welding, hard soldering, or soft soldering. In one embodiment, the substance-to-substance bond is a welded connection. The welded connection can be attained, for example, by using laser welding. By fusing the conductor as part of the welding, the opening in the electrode segment can be closed completely. In one embodiment, additional material can also be welded in order to close the opening completely. The penetration of liquids or of other contaminations into the opening can be avoided thereby. In addition, sharp edges, or burrs of the outside of the opening can thus be overlapped and can thus be smoothed.

In one embodiment, the electrical conductor is connected in a non-positive manner to the electrode segment within the opening. This non-positive connection can be attained by clamping using tweezers, by crimping or swaging (drop-forging) or other mechanical swaging processes, which are known in the technical field. Some suitable processes are described in EP3185248 A1. Comparable processes, which are known to the person of skill in the art in this context, can also be used.

In one embodiment, the electrical conductor is directly connected by using a substance-to-substance bond to the electrode segment within the opening. In one embodiment, the electrical conductor is directly connected in a non-positive manner to the electrode segment within the opening. In one embodiment, the electrical conductor is directly connected by using a substance-to-substance bond as well as directly in a non-positive manner to the electrode segment within the opening. In one embodiment, the electrical conductor is directly connected by using a substance-to-substance bond, but not in a non-positive manner, to the electrode segment within the opening.

The electrical conductor can furthermore also be connected in a positive manner to the electrode segment within the opening. In one embodiment, the electrical conductor is directly connected in a positive manner to the electrode segment within the opening.

In one embodiment, the electrical conductor is connected by using a substance-to-substance bond, but not in a non-positive manner, to the electrode segment. The electrical conductor can also be connected exclusively by using a substance-to-substance bond to the electrode segment. A substance-to-substance bond is in one embodiment a welded connection. Due to an exclusive substance-to-substance bond, a deformation of the electrode segment is avoided and a very stable, permanent and highly conductive connection is simultaneously attained between the conductor and the electrode. This is particularly advantageous when the electrode has a certain surface property and is to also maintain the latter after being contact-connected to the conductor. For example particularly smooth electrode surfaces, which are precisely defined in their geometry, can thus be attained.

In the alternative or in addition to the above-described opening, the electrode can have a structure in the shape of a groove. A line wire can be connected in a non-positive and/or positive manner to the electrode segment in this way, without the line wire having to have a free end for this purpose. For this purpose, the line wire can be clamped and/or welded into the groove. With regard to this, reference is made to the application DE102018221635 by the same applicant, the content of which is hereby incorporated into this application. It is expressly intended that protection is sought in connection with the present embodiment for the structures for connecting the electrode segment to a line wire described in DE102018221635.

A structure can be created, for example, by using laser drilling, laser ablation, laser cutting, spark erosion or chip removal processes. In one embodiment, several segments have a structure, as it is described above. In one embodiment, each of the segments has at least one structure of this type. Each segment is in one embodiment connected to another conductor by using the structure. This makes it possible that each segment can be electrically addressed individually. Different electrical signals can be output or received by several segments independently of one another by using a segmented electrode, in the case of which each segment can be electrically addressed individually, without these signals mutually influencing one another.

When the conductor has several wires, the electrode segments can be connected to one, several, or all wires of a conductor. An electrode segment is in one embodiment connected directly to all wires of a conductor.

In one embodiment, signals can be output in different directions by different electrode segments, or signals can be received from different directions. In one embodiment, the segments are set up and arranged to output signals in different directions, or to receive signals from different directions. In one embodiment, the segments are arranged at different circumferential positions of the electrode segment for this purpose. In one embodiment, the segments are arranged at different radial angles to the main axis of the electrode.

Plastics, which can be used for the insulating areas, include, for example, PET, ETFE, PTFE, FEP, PFA, PU, PI, PEEK, PVDF, a polyolefin, a silicon, or an elastomer. In one embodiment, the shrinkable plastic is PET (polyethylene). In one embodiment, the plastic is a biocompatible plastic.

In one embodiment, the insulating areas have a shrinkable plastic. A shrinkable plastic of this type is characterized in that it significantly reduces its volume in the case of changing ambient conditions. One example for a shrinkable plastic of this type are commercially available shrink tubes, which contract in response to heating. However, the use of a plastic, the volume of which decreases significantly, for example due to a chemical reaction, is also conceivable. Due to the use of a shrinkable plastic, the insulating areas between the electrode segments can be produced so as to fit particularly accurately, i.e. with small clearances and without the creation of sharp burrs or edges. In one embodiment, the electrode segments form an essentially continuous transition with the insulating areas on the outer surface of the electrode, i.e. virtually no gaps or protrusions are present in the boundary area between the electrode segments and the insulating areas. In one embodiment, the electrode segments, together with the insulating areas, form a continuous surface, so that the electrode has an isodiametric shape at least in the area of the electrode segments. This means that the electrode has a consistent diameter in this area.

In one embodiment, the electrode segments are overmolded with a plastic, after they were arranged at the electrode. In one embodiment, excess plastic can be removed by using grinding processes to expose the electrode segments and to establish an isodiametric transition of the surface of the electrode segments to the insulation.

In one embodiment, the insulating areas are elastic, i.e. they have a low elasticity module. In one embodiment, the elasticity module is less than 10 GPa (gigapascal), in one embodiment less than 5 GPa, less than 1 GPa, or less than 0.1 GPa. The elasticity module of a material can be determined in accordance with EN ISO 527-1.

In one embodiment, the insulating areas include a shrinkable plastic with an elasticity module of less than 10 GPa, in one embodiment less than 5 GPa, less than 1 GPa, or less than 0.1 GPa. This plastic is in one embodiment biocompatible.

In one embodiment, the outer surface of the electrode segments additionally has a structure or an increased roughness, which improves the reception or output of an electrical signal. The impedance or the resistance can be reduced, for example, by this structure or increased roughness, in particular in the medically relevant range, for example below 20 kHz. A structure can be used, for example, as it is described in the patent publication number US 2019/0159833A1, which is hereby incorporated completely by reference. Regular linear or flat tip structures, for example, can be used, as they are illustrated therein in FIG. 3A, 3B, or 3C. The surface of the electrode segments and/or of the entire electrode can be coated with conductive metals, metal oxides, or polymers. In the case of the coating of the entire electrode, portions of the coating can subsequently be removed, for example by using laser ablation, in order to electrically separate the segments among one another. In some embodiments, the inside and/or the outside of the electrode segments is micro-structured and/or coated. A micro-structuring and/or coating of this type can effect, for example, a lower impedance or can improve the electrical contact between conductor and electrode, or the contact to the body of a living being. In some embodiments, the inside is micro-structured in order to improve the adhesion to the plastic. The surface can be structured, for example, by using a laser. In one embodiment, the surface is enlarged in that the surface is roughened. This can take place by using various processes, for example by using a laser.

A coating can effect a lower impedance or can improve the electrical contact between conductor and electrode, or the contract to the body of a living being. TiN, Ir, IrO$_x$, Pt or conductive polymers, for example conductive polymers on the basis of thiophene, such as, for example, poly-3,4-ethylenedioxythiophene (PEDOT) or the conductive polymers described in WO/2015/031265, or commercially available polymer compositions, such as Amplicoat or Tecticoat, can be used for a coating of this type. A coating can be carried out, for example, by using PVD, CVD or electrochemical separation.

In one embodiment, the electrode segments are arranged and configured to improve a directional reception or output of an electrical signal. For example, the electrode segments, which are located in spatial proximity to one another in the axial direction, are spaced apart sufficiently in the radial direction, so that the output and/or received electrical signals influence one another as little as possible. Several electrode segments, which are located in the same axial position, can be arranged, for example, essentially equidistantly to one another in the radial direction. Depending on the desired medical application, the individual electrode segments can be positioned as desired on the electrode in the axial as well as in the radial direction. The electrode segments can also be located, for example, only at a radial position along the axis of the electrode. Due to the setup described herein and due to the corresponding production process, it is possible to freely position the electrode segments in the electrode setup essentially independently of one another. This applies for the axial (from distal to proximal) and the radial (circumferential) direction of the electrode.

For example, several electrode segments can also be positioned as group close to one another at a certain point in order to stimulate and/or to analyze a certain target area of the human or animal body in a focused manner. The electrode can have several groups of this type. A group of this type can have, for example, 4, 6, 8, 10, 12, 14, 16. 18, or 20, or more electrode segments.

A tip-shaped electrode segment can additionally be attached at the distal end of the electrode. This electrode segment can likewise have a step, as described herein, or it can be a conventional tip-shaped electrode segment, as it is known in the prior art.

In one embodiment, the edges of the electrode segments are arranged and configured to improve the fatigue behavior of the conductor at the contact point to the electrode segments. For example, the shape of the edges of the electrode segments can be adapted so that they do not harm the conductor, when the electrode is deformed or bent. For example, the edges of the electrode segments can be rounded, can have a geometrical and/or mechanical gradient, or can have other structures, which are adapted to the conductor, such as, for example, notches.

One embodiment relates to a process, which has the following steps:

providing a cable, which has an electrical conductor and an insulation, wherein the insulation surrounds the conductor at least in some sections over its entire circumference;

partially removing the insulation, and thus forming spaces;

providing electrode segments, wherein the electrode segments have steps;

arranging the electrode segments in the spaces, and thus connecting the electrode segments to the insulation in a positive manner; and arranging an insulating material between two adjacent electrode segments, and thus forming insulating areas between the adjacent electrode segments, wherein the insulating areas engage with the steps.

In one embodiment, the steps are performed in the above-mentioned order.

The cable has at least one electrical conductor and an insulation, as it is described above for the embodiments. When the cable has several electrical conductors, for example wires, the insulation can surround all of these individual conductors jointly. In the alternative or in addition, all conductors of the cable can be surrounded by an insulation. The individual conductors of a cable can be stranded together.

Several cables can optionally be stranded together or can be bundled in a different way in order to arrange as many cables as possible within a total diameter, which is as small as possible. In one embodiment, the insulated cables are spirally arranged around a hollow space (referred to as coil structure in the technical field) or a central cable. In one embodiment, the insulated conductors are arranged in the shape of a so-called flat cable, i.e. the insulating conductors are arranged next to one another in one plane. In one embodiment, the insulations are axially welded together are surrounded by a further plastic layer, for example a shrink tube, so that the individual insulated conductors hold together in one plane.

The insulation surrounds the conductor over its entire circumference. The conductor is in one embodiment insulated essentially over its entire length. However, the insulation can in particular be exposed in the area of the contact-connection between the electrical conductor and an electrode segment in order to provide for the electrical connection between conductor and electrode segment. The insulation of the cable is in one embodiment arranged and configured to prevent an unwanted transmission of electrical signals from one cable to another cable. This makes it possible to electrically control the electrode segments independently of one another. In one embodiment, the insulation is arranged and configured to bundle several conductors and/or several cables, i.e. to arrange and to hold them in a space, which is as small as possible. Separate hollow spaces in the base material of the electrode can thus be forgone, i.e. a setup, which is simpler as compared to the prior art, is made possible.

In the area, which is provided for attaching an electrode segment, the insulation of the cable is partially removed. This creates a depression in the insulation of the cable. The electrode segments have steps, as it is described in connection with the embodiments. The depression in one embodiment has a shape, which is complementary to the shape of an electrode segment, so that the electrode segment can be inserted into the depression so as to fit accurately. Protrusions remain in the insulation of the cable in the areas, which have not been removed, i.e. outside of the depressions.

The electrode segments are arranged in the spaces, so that the electrode segments are connected to the insulation in a positive manner.

Together, the protrusions and a surface of the step structure of the electrode in one embodiment form an essentially continuous surface, after the electrode segment is inserted into the depression.

To connect an electrode segment to a conductor, the conductor can initially be insulated at an end of the conductor out of the cable and can be guided to the outside. This end of the conductor can then be electrically and mechanically connected to a structure, for example an opening, in the electrode segment, as it is described herein above in the embodiments. For example, the conductor can be clamped and welded in an opening of the electrode segment.

An insulating material is arranged between two adjacent electrode segments, so that insulating areas are formed between the adjacent electrode segments. The insulating areas thereby engage with the steps, so that a positive connection is formed between the electrode segments and the insulating areas.

The removal of the insulation can take place by using mechanical tools or in a contact-free manner with the help of light, for example with the help of a laser (laser ablation).

In one embodiment, the process includes the forming of a structure on the surface of the electrode segments/or the roughening of the surface of the electrode segments, the improving of the reception or output of an electrical signal, as it is described above in the embodiments. The forming of a structure on the surface of the electrode segments/or the roughening of the surface of the electrode segments can take place by using mechanical tools or in a contact-free manner with the help of light, for example with the help of a laser (laser ablation).

The insulating material can be, for example, a plastic, as it is specified above for the embodiments. In one embodiment, the insulating material is a shrinkable plastic.

With regard to the process, all of the arrangements, materials, and parameters described in the embodiments can be used.

One embodiment relates to an electrode, which can be produced according to a process described herein.

EXAMPLES

One embodiment will be further clarified below on the basis of examples, which, however, should not be understood as being limiting. It will be clear to the person of skill in the art that other equivalent means can be used in a similar way instead of the features described here.

Production of a Segmented Electrode

The electrode segments can be made, for example, of a metal pipe, which is initially brought into the desired basic shape in a drawing process. By cutting the pipe into several ring-shaped parts, electrode segments in the desired length can be created. This can take place with the help of mechanical tools or by using laser cutting processes. The ring-shaped parts can now be axially severed, whereby several electrode segments are created from each ring part. The step structures described herein can be formed at the edges of the individual segments in this step or in a subsequent process step, for example with the help of mechanical tools, laser cutting, or spark erosion. For example, machining processes, for example a milling process, can be used. The surface structure of the pipe/or of the ring-shaped parts can optionally be changed by mechanical or laser-based processes, as it is specified above.

A cable can be made, for example, of insulated metal wire, wherein several insulated metal wires are stranded together and are subsequently surrounded with a plastic insulation. The outer insulating layer thereby surrounds all conductors of the cable. The insulation of the cable can be removed at the desired contact-connection point by using laser ablation or mechanical cutting. Depressions are formed thereby, into which electrode segments can be inserted. The conductor can optionally be severed within the cable, so that a free end of the conductor can be guided out of the cable. If the conductor consists of several wires, all of these wires can be welded together at the cut point so as to be able to connect them more easily to an electrode segment. The free end of the conductor can be guided, for example, through a bore in the electrode segment and can subsequently be clamped therein, for example by crimping or swaging, and/or welded. An insulating material, which separates the electrode segments from one another, is introduced between the individual segments. The introduction of the insulating material can advantageously take place by applying a shrink tube to the electrode. The shrink tube is in one embodiment shrunk, for example under heat, just enough so that it abuts against the electrode surface, but does not yet completely fill all spaces between the electrode segments. The shrink tube can then be removed selectively at those points, at which it covers the surface of the electrode segments. This can take place in an advantageous manner by using laser ablation. In a particularly advantageous embodiment, a modification of the surface of the electrode segments can take place in the same process step by using laser ablation. The shrink tube can then be shrunk completely, so that it completely fills the spaces between the electrode segments, i.e. continuous insulating areas are formed between the electrode segments. The thickness of the shrink tube is in one embodiment selected accordingly, so that an isodiametric electrode is formed by the final shrinking of the shrink tube. This thickness depends on the material-specific shrinking behavior of the used plastic, and on the dimensions of the step structure of the electrode segment, and can be determined with the help of simple test series. Together with the insulating areas, the electrode segments in one embodiment form a common surface in this way, which essentially does not have any sharp edges and burrs.

The embodiments described herein are not limited to the use of a shrink tube, but other processes for introducing the insulating material can alternatively also be used, for example injection molding processes, as they are known and common in the prior art. With the use of the step structure, an improved stability can also be attained when using these alternative processes. With the use of a shrinkable plastic, however, a particularly simple and cost-efficient production is possible, because no specifically produced injection molding tool is required.

FIG. 1 illustrates an embodiment of a segmented electrode 100 in an exemplary manner. The electrode 100 includes one or several conductors 101. Each of the conductors includes an insulation, so that the conductors are electrically insulated from one another. Several conductors 101 can be bundled to form a cable. An insulation 102 surrounds all conductors 101 of the electrode 100 collectively. Some parts of the insulation 102 form protrusions 103, which extend to the outside of the electrode. Electrode segments 104 are arranged between the protrusions 103. The electrode segments 104 include steps 106, which in each case divide the electrode segments 104 into an outer part 111 and an inner part 112. This division is illustrated in FIG. 1 by a dashed line. The inner part 112 of the electrode segment 104 is covered with an insulating area 105 on the side arranged to the outside, so that the electrode segment is held in place. The insulating area 105 thereby engages with the step 106 of the electrode segment 104. This creates a positive connection of the electrode segment 104 with the insulating area 105.

A conductor 101 is insulated from the cable and is guided through a structure 107 in the electrode segment 104. The structure 107 can be, for example, a cylindrical bore in the electrode segment 104. The conductor 101 is attached in the structure 107 by clamping and/or welding in order to form a stable electrical and mechanical connection between the conductor 101 and the electrode segment 104. A structure 109 on the outer part 111 of the electrode segment 104 increases the surface of the electrode segment and thus improves the electrical properties of the electrode. For example a smaller resistance, a lower impedance, or a better contact-connection of the body tissue, which is to be contact-connect, can be attained thereby. The structure 109 can thereby extend over the complete outer surface of the electrode segment 104 or over a portion thereof. Several areas including structures 109 can also be arranged on a surface of an electrode segment 104.

The following figures illustrate the performance of a process for producing a segmented electrode of this type in an exemplary manner. The process can optionally be modified by one or several of the embodiments described herein.

For this purpose, a cable is initially provided, which has an electrical conductor 101 and an insulation 102, wherein the insulation 102 surrounds the conductor 101 at least in some sections over its entire circumference.

Figure 2:
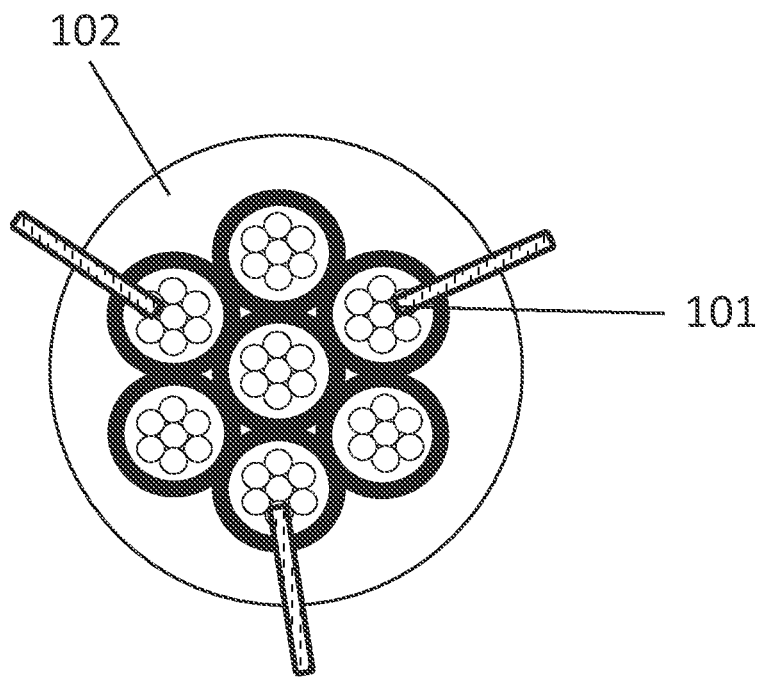
FIG. 2 illustrates a cable, wherein individual conductors are guided out of the cable.

FIG. 2 illustrates a cable, which includes several conductors 101. Together, all conductors are surrounded by an insulation 102. A conductor can consist of one or several wires and a further insulation, which surrounds an individual conductor. Individual, several, or all wires of a conductor 101 are insulated from the conductor 101 and are guided to the outside. To insulate a wire from a conductor 101, the wire is severed and a free of the wire created thereby is guided out of the conductor 101 to the outside by using a suitable tool, for example a needle. The insulation 102 is partially removed, for example with the help of laser ablation, so that protrusions 103 are formed therein, between which spaces 110 are arranged. These spaces 110 are depressions, which are formed by removal of the insulation. They in one embodiment have a shape, which is complementary to the electrode segments.

Figure 3:
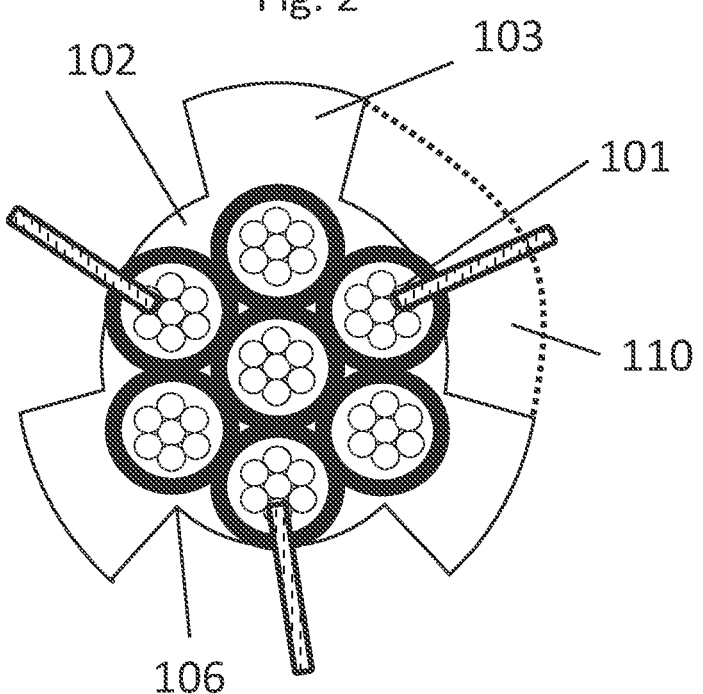
FIG. 3 illustrates a cable, wherein the insulation is partially removed.

FIG. 3 illustrates a cable, in the case of which the insulation 102 is removed in this way.

The removed portion of the insulation 102 is illustrated by a dashed line.

Figure 4:
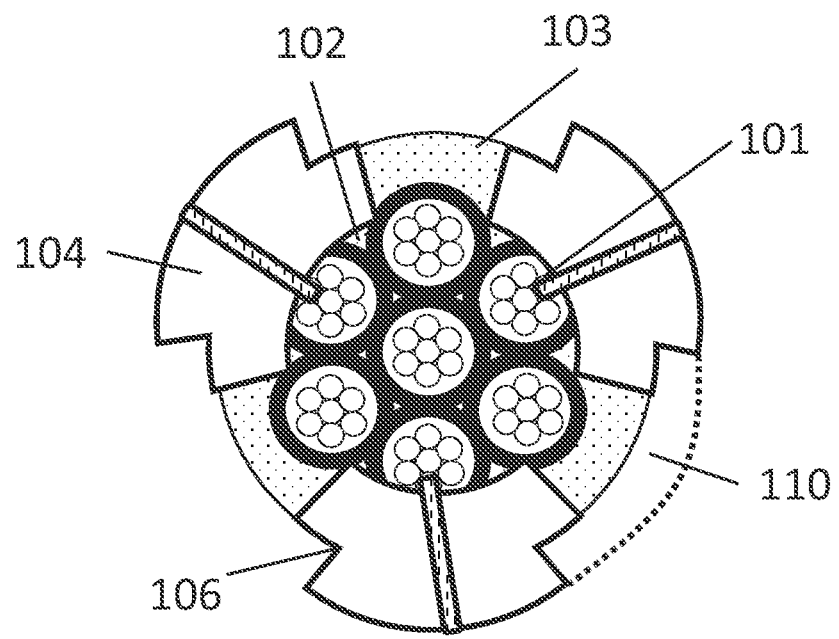
FIG. 4 illustrates a cable having electrode segments.

Electrode segments 104 are subsequently inserted into the spaces 110. FIG. 4 illustrates the intermediate product of an electrode, in the case of which the electrode segments are attached to the cable in the area of the spaces 110. Several conductors 101 are guided through the electrode segments 104 to establish a contact-connection, i.e. an electroconductive connection, of the conductors 101 to the electrode segments 104.

Figure 5:
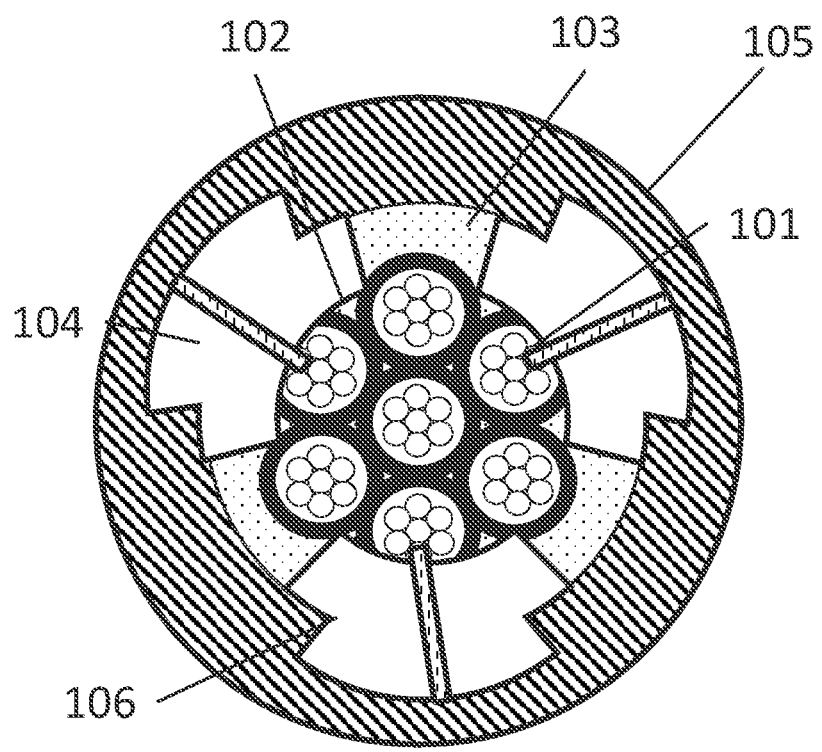
FIG. 5 illustrates a cable into which an insulating material is introduced into the spaces between the electrode segments.

An insulating material is subsequently applied between the electrode segments 104, so that insulating areas 105 are formed between the electrode segments 104. FIG. 5 illustrates an intermediate product of an electrode, in the case of which the insulating areas 105 are already formed.

The insulating material can be, for example, a shrinkable plastic, which can be attached, for example as shrink tube, over the entire cable or over a partial area thereof. Due to the shrinkage, for example a heat-induced shrinkage, the material wraps tightly around the cable or electrode intermediate product, respectively. The insulating material thereby covers the inner part 112 of the electrode segments 104.

Excess material, which covers, for example, the outer part 111 of the electrode segments 104, can be removed, so that the outer surface of the electrode segments 104 is accessible to the outside.

Figure 6:
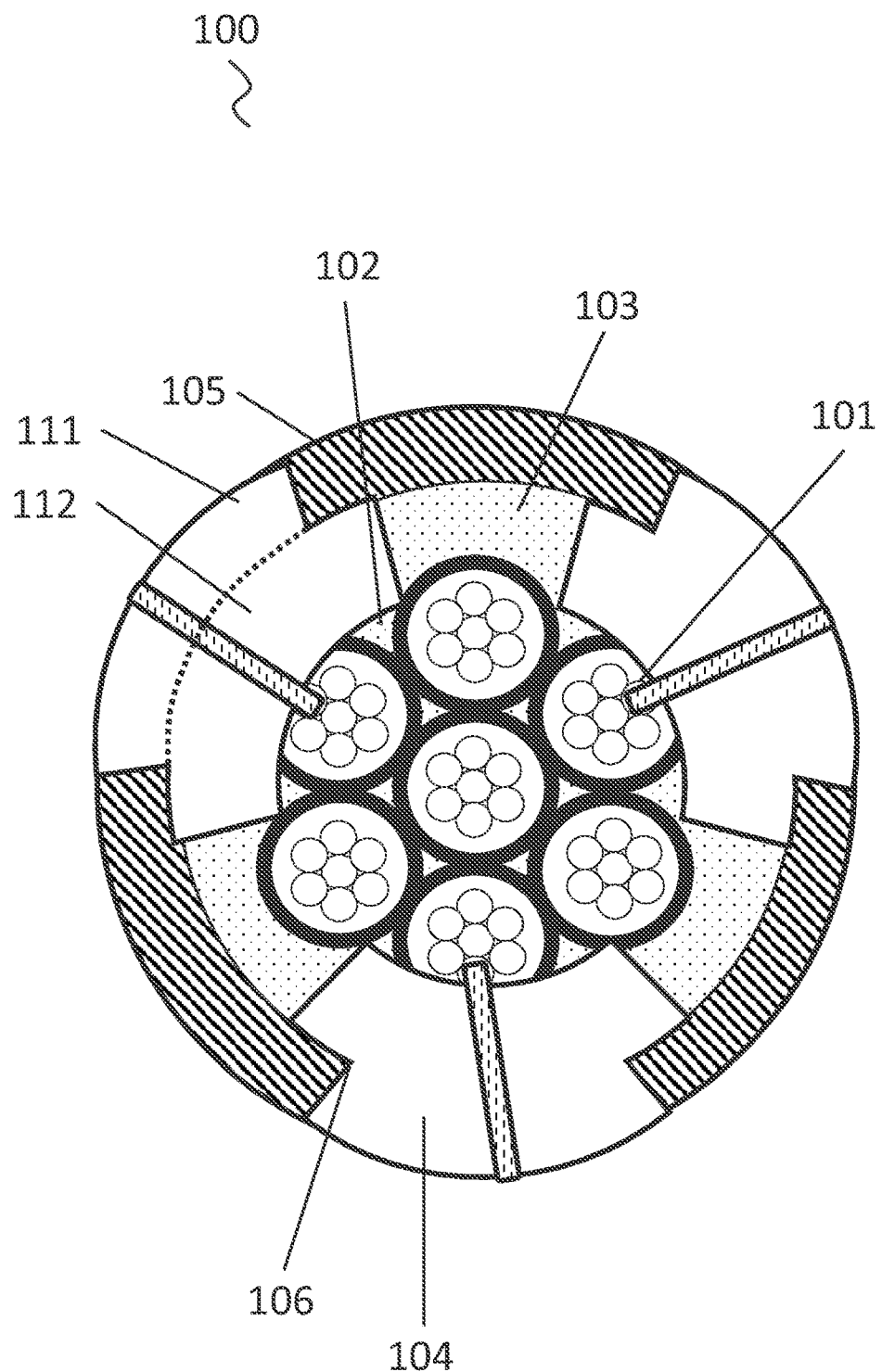
FIG. 6 illustrates an electrode in which the insulating material is removed, so that the surface of the electrode segments is exposed.

In the alternative, other insulating materials and suitable coating processes can be used, for example extrusion or overmolding. FIG. 6 illustrates an electrode 100, in the case of which the surface of the outer part 111 of the electrode segments 104 has been exposed, because excess portions of the insulating areas 105 are removed. The insulating areas 105 only still cover the inner part 112 of the electrode segments 104, in particular in the area of the steps 106. A positive connection is formed at this point. The insulating areas 105 abut laterally against the outer parts 111 of the electrode segments 104 and form a common surface, which is essentially free from burrs and edges.

Figure 7:
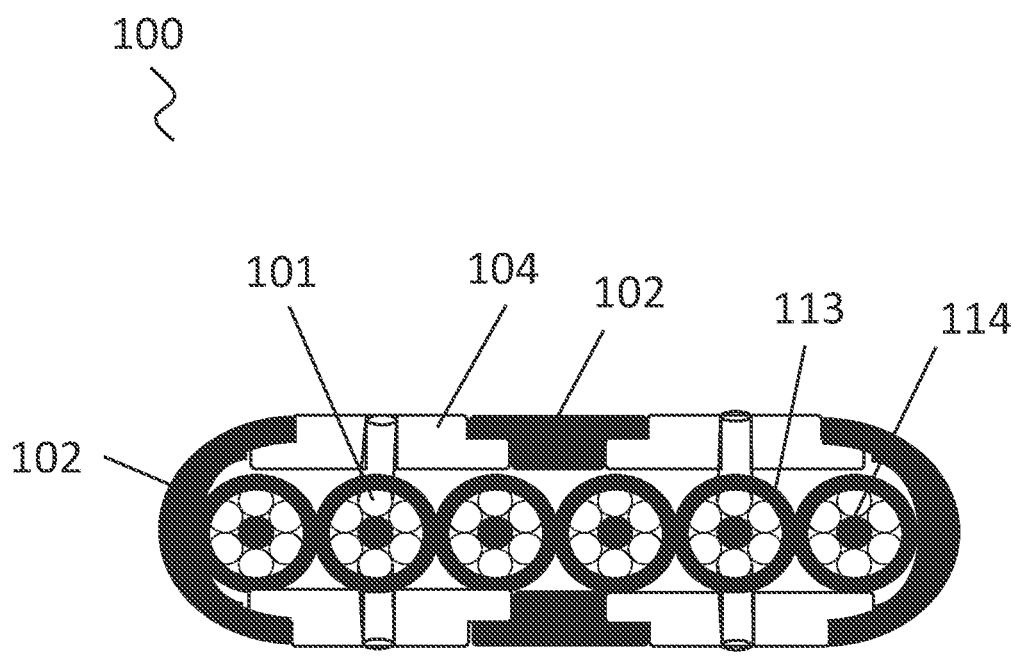
FIG. 7 illustrates an electrode in which several conductors are combined to form a conductor bundle.

FIG. 7 illustrates an electrode 100, in the case of which several conductors 101 are in each case combined to form a conductor bundle 113. A conductor bundle 113 of this type can include an insulation, which surrounds the entire conductor bundle 113. A conductor bundle can furthermore include an internal element 114. The internal element 114 can be arranged, for example, centrally in the conductor bundle 113. The internal element 114 can be surrounded by several conductors 101. Together, several conductor bundles 113 can be arranged to form a cable, which can have an essentially round (as illustrated in the preceding figures) or a flat geometry. A flat geometry of this type is illustrated in FIG. 7. The conductor bundles 113 are thereby arranged next to one another in one plane. In one embodiment, the insulations of the conductor bundles are welded together or are surrounded with a further plastic layer, for example a shrink tube, so that the individual conductor bundles are arranged and fixed in one plane. The entire cable is surrounded by an insulation 102. Electrode segments 104, which are connected to a conductor 101, are arranged in the insulation 102, as it is described in detail above herein. Electrode segments can be arranged at arbitrary points along the conductors.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof.

The invention claimed is:

1. A medical electrode comprising:
a cable arranged along a central longitudinal axis of the medical electrode, the cable comprising a conductor;
an insulation, which surrounds the cable at least in some sections over an entire circumference of the cable;
protrusions in the insulation extending toward an outer surface of the medical electrode thereby defining spaces between the protrusions;
electrode segments arranged directly on the insulation of the cable between the protrusions and in the spaces, the electrode segments each comprising an inner part and an outer part, the outer part comprising at least a portion of the outer surface of the medical electrode and wherein the inner part is wider than the outer part in a radial direction of the each electrode segment thereby forming a step;
wherein the protrusions extend radially outward and each protrusion has a protrusion outer surface that aligns radially with the inner part of two adjacent electrode segments thereby forming a protrusion formation between outer parts of the two adjacent electrode segments; and
insulating areas separate from the insulation surrounding the cable and arranged between the outer parts of two adjacent electrode segments and radially outside of the inner parts of two adjacent electrode segments, and the insulating areas forming a portion of the outer surface of the medical electrode, at least one insulating area overlapping the step and the inner part of at least two of the electrode segments and one protrusion such that the at least one insulating area holds the electrode segments in place.

2. The medical electrode according to claim 1, wherein the electrode segments comprise a plurality of electrode segments and wherein the conductor comprises a plurality of conductors, wherein different electrode segments are in each case electrically connected to different conductors.

3. The medical electrode according to claim 1, wherein the electrode segments have a structure configured to facilitate the connection of the conductor to an electrode segment.

4. The medical electrode according to claim 3, wherein the structure is an opening or a groove.

5. The medical electrode according to claim 1, wherein the conductor is connected to an electrode segment by means of a substance-to-substance bond and/or in a positive manner.

6. The medical electrode according to claim 1, wherein the insulating areas include a shrinkable plastic.

7. The medical electrode according to claim 1, wherein the electrode segments, together with the insulating areas, form a continuous surface, so that the medical electrode has an isodiametric shape at least in an area of the electrode segments.

8. The medical electrode according to claim 1, wherein the outer part of the electrode segments furthermore has a structure, and/or has an increased roughness, wherein the structure and/or increased roughness improves the reception or output of an electrical signal.

9. The medical electrode according to claim 1, wherein the electrode segments are arranged and configured to improve a directional reception or output of an electrical signal.

10. The medical electrode according to claim 1, wherein edges of the electrode segments are arranged and configured to improve the fatigue behavior of the conductor at a contact point to the electrode segments.

11. The medical electrode of claim 1, wherein the electrode segments are arranged exclusively between the protrusions, such that no portion of the electrode segments are directly radially above the protrusions of the medical electrode.

12. The medical electrode of claim 1, wherein the insulating areas arranged between the outer parts of two adjacent electrode segments and radially outside of the inner parts of two adjacent electrode segments are additionally configured to abut the outer part of the electrode segment such that both of the outer part of the electrode segment and the insulating areas form the outer surface of the medical electrode.

13. A process for producing the medical electrode of claim 1 comprising:
  (i) providing the cable, which has the conductor and the insulation, wherein the insulation surrounds the conductor at least in some sections over its entire circumference;
  (ii) partially removing the insulation, and thus forming the spaces;
  (iii) providing the electrode segments, wherein the electrode segments have steps;
  (iv) arranging the electrode segments in the spaces, and thus connecting the electrode segments to the insulation in a positive manner; and
  (v) arranging an insulating material between two adjacent electrode segments, and thus forming the insulating areas between the adjacent two electrode segments, wherein the insulating areas engage with the steps.

14. The process according to claim 13, wherein the process further comprises forming a structure on the outer parts of the electrode segments or roughening the outer parts of the electrode segments to improve the reception or output of an electrical signal.

15. The process according to claim 14, wherein the partial removing of the insulation and/or the forming of a structure on the outer parts of the electrode segments, and/or the roughening of the outer parts of the electrode segments, is performed using a laser.

16. The process according to claim 13, wherein the insulating material has a shrinkable plastic.

* * * * *